United States Patent [19]

Gardner

[11] 4,359,427

[45] Nov. 16, 1982

[54] PROCESS FOR PRODUCING PEROXYDICARBONATES

[75] Inventor: Keith L. Gardner, Avon, Ohio

[73] Assignee: The B. F. Goodrich Company, Akron, Ohio

[21] Appl. No.: 286,945

[22] Filed: Jul. 27, 1981

[51] Int. Cl.³ ............................................ C07C 179/18
[52] U.S. Cl. .................................................. 260/463
[58] Field of Search ........................................ 260/463

[56] References Cited

U.S. PATENT DOCUMENTS

| | | | |
|---|---|---|---|
| 3,377,373 | 4/1968 | Lederer et al. | 260/463 |
| 3,429,910 | 2/1969 | Lederer et al. | 260/463 |
| 3,657,311 | 4/1972 | D'Angelo | 260/463 |
| 3,720,700 | 3/1973 | Norback | 260/463 |
| 3,821,273 | 6/1974 | D'Angelo | 260/463 |
| 3,950,375 | 4/1976 | McKee et al. | 260/463 |
| 4,137,252 | 1/1979 | Komai et al. | 260/463 |

Primary Examiner—Donald G. Daus
Assistant Examiner—M. C. Eakin
Attorney, Agent, or Firm—Joe A. Powell; Alan A. Csontos

[57] ABSTRACT

The invention covered relates to an improved, solvent-free process for the continuous manufacture of peroxydicarbonate polymerization catalysts. The improvement in the process is the mere decanting of the reaction product through a filtering medium into a separation zone, decanting to a washing zone, decanting to a second separation zone and then taking the product up in an aqueous medium containing a suitable emulsifying agent whereby the resultant initiator or catalyst emulsion can be conveniently and safely stored until ready for use in a polymerization reaction.

13 Claims, No Drawings

PROCESS FOR PRODUCING PEROXYDICARBONATES

BACKGROUND OF THE INVENTION

Peroxydicarbonates have the general formula RO—C(O)—O—O—C(O)—OR wherein R is an alkyl group. These compounds are important for use as free radical producing initiators in the polymerization field, and particularly in the polymerization of vinyl monomers. However, the peroxydicarbonates have one serious disadvantage, and that is their inherent instability. They are sensitive both thermally and to heavy shock and some of them are capable of detonating under certain conditions. Accordingly, it is necessary to take precautions during manufacture thereof in order to prevent decomposition from either heat or shock.

In the past, peroxydicarbonates were made by batch processes where large amounts were handled in order to be economical. However, under such circumstances, explosions have occurred in trying to make a pure product. One answer was to use diluents or inert solvents in the process and then sell a dilute product. This did not completely solve the problem since, in many polymerization processes, it is desirable to use the pure, undiluted product.

It was thereafter proposed to produce the peroxydicarbonates continuously. For example, see U.S. Pat. No. 3,377,373, issued Apr. 9, 1968, wherein the patentees react a chlorocarbonic acid ester with hydrogen peroxide and an aqueous alkali metal hydroxide solution in at least two reaction zones. The reaction is thereafter terminated in an after-reaction zone by addition of a halogenated organic solvent. The solvent solution is then isolated by using various settling vessels, or washing vessels. A similar process using solvents is described in U.S. Pat. No. 3,429,910, issued Feb. 25, 1969. However, when using an organic solvent diluted initiator in a polymerization process, problems arise. First, when using an organic solvent, it has a tendency to remain in the polymer being produced, which, in turn, makes drying of the polymer more difficult. Further, due to the flammability of such organic solvents, removal thereof from the polymer is dangerous and costly. Also, the flammability of organic solvents presents a serious safety problem in storage and handling when they are used as carriers for unstable initiators.

The use of solvents in making the initiators decreases the efficiency of processing. Further, for many polymerization processes, pure peroxydicarbonates are desired. Accordingly, it is most desirable to have a continuous, solvent-free process for making peroxydicarbonates which will increase processing efficiency.

SUMMARY OF THE INVENTION

The present invention relates to an improved solvent-free process for the continuous manufacture of peroxydicarbonates by continuously reacting chloroformate, having the formula RO—C(O)—Cl, wherein R is an alkyl group containing from 3 to 16 carbon atoms, with aqueous hydrogen peroxide and an aqueous alkali metal hydroxide at a temperature in the range of about 0° C. to about 40° C. in one or more reaction zones. The improvement in the present process is the mere decanting of the reaction product through a filtering medium into a separation zone, decanting to a washing zone, decanting to a second separation zone and then taking the product up in an aqueous medium containing a suitable emulsifying agent whereby the resultant initiator emulsion can be conveniently and safely stored until ready for use in a polymerization reaction.

DETAILED DESCRIPTION

It has been found that peroxydicarbonates can be continuously produced in high purity and safely in a solvent-free process without the use of centrifuges to isolate the pure product, such as are used in the process described in U.S. Pat. No. 3,950,373 issued Apr. 13, 1976, in the name of McKee. One of the unique features of the present process is the separation of the reaction product by a simple decantation which relies on the density differential between the organic product, peroxydicarbonate, and the aqueous waste. While the reaction can be accomplished with one reaction vessel or reactor in the reaction zone, it is preferred to employ more than one reactor since this increases the dwell time of the reaction mixture in the reaction zone which insures more complete reaction with resulting increased yields. When more than one reactor is employed, the reaction mixture is continuously decanted from one reactor to the next.

The reaction of the chloroformate, aqueous hydrogen peroxide and aqueous alkali metal hydroxide is carried out in the reaction zone at a temperature in the range of about 0° C. to about 40° C. Preferably, the temperature of reaction is maintained in the range of about 10° C. to about 25° C. The temperature of reaction is maintained by the use of jacketed reactors through which is circulated a suitable liquid coolant, such as cold water, brine, and the like. The time of reaction will vary, depending upon the yield desired, but normally will be in the range of about 5 minutes to about 30 minutes. It should be noted that when more than one reactor is employed, the temperature in each reactor may be varied when the temperature increases due to the nature of the reaction. However, any such differential in temperature will still be within the overall temperature range given above.

From the reaction zone the reaction mixture is decanted through a gravity filter into a separation zone. The filter medium is a cloth filter or a glass wool filter, and the like. Suitable cloth filters are those made of cotton, rayon, nylon, polyester fibers or filaments, acrylic fibers, and the like. The purpose of filtering is to remove the excess sodium peroxide, which is an orange solid, from the reaction mixture. From the filter, the reaction mixture is fed into a separator vessel or tank which is jacketed so as to regulate the temperature therein. After separation, the upper organic layer containing the catalyst is decanted into a wash tank equipped with an agitator and jacketed. Demineralized water is added to the liquid organic material with agitation. The purpose of the washing is to remove inorganic by-products, such as alkali metal chlorides, e.g., sodium chloride, and any alkali metal peroxide that may have come through the filter, e.g., sodium peroxide. After washing, the material is decanted into a second separator tank which is jacketed wherein the liquid catalyst is separated from the water containing the inorganics. The temperature in the separation zone is maintained in the range of about 5° C. to about 15° C.

The finished product or catalyst is decanted from the last separator to a recovery or take-up zone. One novel feature of the present process is that the product is immediately dispersed in an aqueous solution containing one or more water-soluble dispersants. In a vessel or tank that is jacketed, or contains cooling coils, and equipped with an agitator, a solution is made of one or more surfactants in demineralized water. While vigorously agitating the solution, the catalyst is decanted therein thus forming a dispersion or emulsion of the catalyst in the form of tiny droplets or particles. Any of the usual dispersants employed in the suspension polymerization of vinyl monomers may be used in the aqueous catalyst dispersion or emulsion. As examples of said dispersants there may be named the hydrolyzed polyvinyl acetates wherein the hydrolysis is in the range of about 70% to about 90%, alkyl and hydroxyalkyl cellulose ethers, such as methyl cellulose, hydroxypropyl methyl cellulose, and the like, gelatine, polyvinylpyrrolidone, etc., polyoxyethylene sorbitan monolaurate, and like compounds, etc. The dispersants may be used in combination, if desired. The amount of dispersant(s) employed in the catalyst dispersion will usually be in the range of about 0.5% to about 10.0% by weight. It is preferred, however, to employ the dispersant(s) in the range of about 1.0% to about 5.0% by weight. While the amount of catalyst in the dispersion or emulsion may vary over a wide range of concentration, as a practical matter, an emulsion containing from about 10% to about 30% by weight of catalyst is satisfactory.

After recovery, or take off of the catalyst, in the form of an aqueous dispersion, the same is sent to storage for future use in polymerization reactions. Of course, the catalyst dispersion can be used immediately, if the polymerization production line is ready for it. The catalyst dispersions are capable of being safely stored as such without agitation, due to their stability, for appropriate periods of time commensurate with efficient plant operation. When stored, the catalyst dispersions are stored at a temperature in the range of about 0° C. to about 10° C. Preferably, the dispersions are stored at a temperature in the range of about 2° C. to about 6° C.

Various catalysts can be made by the process of the present invention. The nature, or structure of the catalyst produced will depend upon the particular chloroformate employed in the reaction. Chloroformates having the formula RO—C(O)—Cl wherein R is an alkyl group containing from 3 to 16 carbon atoms, are suitable for use in the present invention. Two particularly useful catalysts are di (secondary butyl) peroxydicarbonate (SPB) and di(2-ethyl hexyl) peroxydicarbonate (EHP). These catalysts are liquid and thus ideally suited for manufacture by the present process. They are widely used in the industry in the suspension polymerization of vinyl monomers. As examples of the vinyl monomers, there may be named the vinyl halides, such as vinyl chloride, vinyl bromide, etc.; vinylidene halides, such as vinylidene chloride, and the like; acrylic acid; esters of acrylic acid, such as methyl acrylate, ethyl acrylate, butyl acrylate, octyl acrylate, cyanoethyl acrylate, and the like; methacrylic acid; esters of methacrylic acid, such as methyl methacrylate, butyl methacrylate, and the like; vinyl acetate; acrylonitrile; styrene and styrene derivatives including α-methyl styrene, vinyl toluene, chlorostyrene, vinyl naphthalene; and other vinylidene monomers having at least one terminal $CH_2=C<$ grouping; mixtures of any of these types of monomers; and other vinylidene monomers of the types known to those skilled in the art. The catalysts of the present invention are particularly useful in the suspension polymerization of vinyl chloride to make polyvinyl chloride (PVC).

In order to further illustrate the present invention, the following specific example is given. It is to be understood, however, that this is merely intended in an illustrative and not limitative sense. In the example, all parts and percents are by weight unless otherwise indicated.

EXAMPLE I

In this example di(secondary butyl) peroxydicarbonate (SBP) was made in a continuous manner to demonstrate the process of the present invention. Three jacketed reactors in series were employed maintaining a 300 ml. working volume in each reactor. The temperature in each reactor was maintained at 25° C. The reaction ingredients namely sodium hydroxide, hydrogen peroxide and secondary butyl chloroformate, were continuously fed into the first reactor at the rates shown in the table appearing hereinafter. The reaction mixture was continuously decanted from one reactor to the next. The time of the reaction, or combined dwell time in the three reactors, was 12 minutes. From the last reactor, the reaction mixture was decanted through a glass wool filter into a separation vessel. The filter removed the excess $Na_2O_2$. The separation vessel was jacketed and the temperature therein maintained at 5° C. After separation, the upper organic layer containing the SBP was decanted into a washing vessel that was jacketed and equipped with an agitator wherein demineralized water was added to the liquid organic material with agitation to remove the inorganic by-products from the organic material. The washing was done at 5° C. After washing, the material was decanted into a second jacketed separator vessel wherein the liquid SBP was separated from the water containing the inorganic by-products. The temperature was maintained at 5° C. After separation, the SBP was decanted into a previously-prepared aqueous solution of 3% by weight of 88% hydrolyzed polyvinyl acetate which was vigorously agitated at 5° C. to give an emulsion of SBP therein containing 25% SBP. A portion of the SBP was collected apart from the emulsion in order to perform an assay thereon. The entire continuous process, or run, was continued for a period of 3 hours. Thereafter, five further runs were made in like manner. The experimental data from the six runs are given in the following table:

TABLE I

| RUN NO. | SODIUM HYDROXIDE - 20% Gms./Min. | HYDROGEN PEROXIDE - % Gms./Min. | SECONDARY BUTYL CHLOROFORMATE Gms./Min. | SBP PRODUCTION Gms./Hr. | SBP YIELD (%) | SBP ASSAY (%) |
|---|---|---|---|---|---|---|
| 1 | 39.1 | 10.6 (32%) | 15.0 | 268 | 70.0 | 100 |
| 2 | 36.0 | 9.6 (32%) | 15.0 | 548 | 70.6 | 100 |
| 3 | 30.0 | 8.5 (38%) | 18.0 | 489 | 70.0 | 97 |
| 4 | 30.0 | 8.5 (38%) | 18.0 | 489 | 70.0 | 97 |
| 5 | 30.0 | 8.5 (38%) | 14.0 | 616 | 79.5 | 95 |
| 6 | 24.0 | 6.4 (38%) | 15.5 | 564 | 72.0 | 94 |

The above results clearly show that a good pure catalyst can be obtained by the present process wherein a solvent is not needed and homogenization is not necessary. The % yield values appeared to be low because it was difficult to measure the small amounts involved.

In addition to elimination of solvents and homogenization, the present invention has the additional advantage of enhancing the safety of the operation. That is, the final product, or catalyst, is immediately emulsified or dispersed in an aqueous solution. This also enhances the handling and storage of the catalysts. Numerous other advantages of the invention will be apparent to those skilled in the art.

While the present invention has been described in terms of its specific embodiments, certain modifications and equivalents will be apparent to those skilled in the art and are intended to be included within the scope of the present invention, which is to be limited only by the reasonable scope of the appended claims.

I claim:

1. A process for the continuous production of liquid peroxydicarbonates consisting essentially of continuously reacting in one or more reaction zones a chloroformate having the formula RO—C(O)—Cl, wherein R is an alkyl group containing from 3 to 16 carbon atoms, an aqueous hydrogen peroxide and an aqueous alkali metal hydroxide at a temperature in the range of about 0° C. to about 40° C., continuously decanting the reaction mixture through a gravity filtering zone into a separation zone wherein the mixture is separated into a liquid organic layer containing the reaction product and a water layer, decanting said liquid organic layer into a washing zone and washing the same with water, decanting into a second separation zone to separate the washed organic layer, and decanting said organic layer into an agitated aqueous solution containing from about 0.5% to about 10.0% by weight of an emulsifier, thereby forming an emulsion containing the peroxydicarbonate.

2. A process as defined in claim 1 wherein the chloroformate is secondary butyl chloroformate.

3. A process as defined in claim 1 wherein the chloroformate is 2-ethyl hexyl chloroformate.

4. A process as defined in claim 1 wherein the emulsifier is 88% hydrolyzed polyvinyl acetate.

5. A process as defined in claim 1 wherein the filtering zone comprises a glass wool filtering medium.

6. A process as defined in claim 1 wherein the alkali metal hydroxide is sodium hydroxide.

7. A process as defined in claim 1 wherein there are three reaction zones.

8. A process as defined in claim 7 wherein the temperature in the reaction zones is maintained at 25° C.

9. A process as defined in claim 8 wherein the emulsifier is 88% hydrolyzed polyvinyl acetate.

10. A process as defined in claim 9 wherein the filtering zone comprises a glass wool filtering medium.

11. A process as defined in claim 10 wherein the chloroformate is secondary butyl chloroformate.

12. A process as defined in claim 11 wherein the aqueous alkali metal hydroxide is a 20% by weight solution of sodium hydroxide.

13. A process as defined in claim 1 wherein the emulsion contains from about 10% to about 30% by weight of peroxydicarbonate.

* * * * *